United States Patent [19]

Dunlap et al.

[11] Patent Number: 5,382,519
[45] Date of Patent: Jan. 17, 1995

[54] PERIPLASMIC 3':5'-CYCLIC NUCLEOTIDE PHOSPHODIESTERASE AND RELATED METHODS FOR PRODUCING AND USING THE SAME

[75] Inventors: Paul V. Dunlap; Sean M. Callahan, both of Woods Hole, Mass.

[73] Assignee: Woods Hole Oceanographic Institution, Woods Hole, Mass.

[21] Appl. No.: 4,751

[22] Filed: Jan. 13, 1993

[51] Int. Cl.$^6$ .................... C12N 15/31; C12N 15/53; C12N 15/70

[52] U.S. Cl. .................... 435/69.1; 435/196; 435/199; 435/252.33; 435/320.1; 536/23.2; 536/23.7

[58] Field of Search ............... 536/23.2, 23.7; 435/320.1, 252.3, 69.1, 199, 196, 252.33

[56] References Cited

U.S. PATENT DOCUMENTS 5,082,785  1/1992  Manning .................. 435/252.32

OTHER PUBLICATIONS

Young et al. (1983) Proc. Natl. Acad. Sci. 80, 1194–1198.
Lacombe et al. (1986) J. Biol. Chem. 261, 16811–16817.
Callahan et al. (1993) Abstracts of the General Meeting of the American Society for Microbiology, p. 269.
Dunlap et al. (1993) Abstracts of the General Meeting of the American Society for Microbiology, p. 269.
Alper & Ames, Journal of Bacteriology, 122:1081–1090 (1975).
Ames et al., Journal of Bacteriology, 160:1181–1183 (1984).
Barfield et al., Microbiol. Enzymes in Aquatic Environment, Springer Berlay, 1991, pp. 234–248.
Beacham and Garrett, J. Gen. Micro., 119:31–34 (1980).
Botsford, Journal of Microbiology, 160:826–830 (1984).
Botsford, Microbiological Reviews, 45:620–642 (1981).
Buettner et al., Journal of Bacteriology, 114:1068–1073 (1973).
Bullock et al., Biotechniques, 5:376–379 (1987).
Devroetes, Science, 245:1054–1058 (1989).
Dunlap et al., J. Gen. Microbiol. 138:115–123 (1992).
Francko, Advances in Cyclic Nucleotide Research, pp. 97–117 (1983).
Bengis-Garber, Can. J. Microbiol., 31:543–548, 1985.
Monard et al., Biochemical and Biophysical Research Communications, 35:584–591 (1969).
Robison et al., Cyclic Amp, Academic Press, New York (1971).
Ruby et al., Biol. Bull., 151:574–586 (1976).
Saier et al., J. of Biological Chemistry, 250:7593–7601 (1975).
Sambrook et al., Molecular Cloning, Cold Spring Harbor Lab. (1989).
Sanger et al., Proc. Natl. Acad. Sci., 74:5463–5467 (1977).
Silhavy et al., Experiments with Gene Cloning, Cold Spring Laboratory (1986).
Simon et al., Meth. Enzymol., 118:640–659 (1986).
Ullman & Danchin, Advances in Cyclic Nucleotide Research, 15:1–52 (1983).

*Primary Examiner*—Keith Baker
*Attorney, Agent, or Firm*—Linda M. Buckley; Peter F. Corless; David S. Resnick

[57] ABSTRACT

Novel substantially pure periplasmic 3':5'-cyclic nucleotide phosphodiesterases are provided which are obtainable from gram negative bacterium capable of growing on restricted media containing cAMP or cGMP as a sole carbon source. Also provided is the isolated DNA coding for such enzymes and related methods of producing the same.

18 Claims, 4 Drawing Sheets

SDS-PAGE OF ACETONE PURIFICATION OF CpdP PROTEIN

```
    AGTAGAACTATCAAATTCTGTGGAGCATACCGCTTATAATTACCTTCTTATCAATAGTCTTAAATATTAATACATC

78 ATTCATTTATCTCATTGTATTCTGATTGAGCACAAGGTGTGCAGTATTATTAAGGTTGGAT ATG TTT AAA
                           -10                                      SD       Met Phe Lys

152 AAT AAA TTA GCA GTG TTA TTT ACG TGT TTG TCT GTA TTT TCT TTT TCG GCT
    Asn Lys Leu Ala Val Leu Phe Thr Cys Leu Ser Val Phe Ser Phe Ser Ala

203 CAA TCT→GGG AGT TTT GAT ACC GTT ACG GTT TTA TTA GGG GGT ATT CAA
    Gln Ser Gly Ser Phe Asp Thr Val Thr Val Leu Leu Gly Gly Ile Gln

254 GAT GGT AAT TTA ACG TTT GCT TCT GAT GAG GCG GAT TCT TCA AAT TTT
    Asp Gly Asn Leu Thr Phe Ala Ser Asp Glu Ala Asp Ser Ser Asn Phe

305 GTT ATG CTT GAT GCA TTT TCT GTT AAT GGA GTT ATT TCA TCA GAG CAG
    Val Met Leu Asp Ala Phe Ser Val Asn Gly Val Ile Ser Ser Glu Gln

356 AAA GGA TTT AAA TTA GAT AAG ATT CCA AAG GAT TCG TTT TAC ACC AAA
    Lys Gly Phe Lys Leu Asp Lys Ile Pro Lys Asp Ser Phe Tyr Thr Lys

407 GTA GGT TAC CTA TTA AGG TTA TAC TAC TTT ATT CCT ATT AGT CAT GCT
    Val Gly Tyr Leu Leu Arg Leu Tyr Tyr Phe Ile Pro Ile Ser His Ala

458 CAT GAC GTT CAT GTT TTA GCG TTA TCT TCT TTT CCT GAT GAC AGT AAA
    His Asp Val His Val Leu Ala Leu Ser Ser Phe Pro Asp Asp Ser Lys

509 AAA CCG TAT GCA TGG AAT GCA ACA AAT GGT CTC ATG AAG AAT TAC AAA
    Lys Pro Tyr Ala Trp Asn Ala Thr Asn Gly Leu Met Lys Asn Tyr Lys

560 TTT AAT TCA GCA TAT TTT CCT CAA AAC GGT GAA GGC TTT GGT AGT AAA
    Phe Asn Ser Ala Tyr Phe Pro Gln Asn Gly Glu Gly Phe Gly Ser Lys

611 CTG AAC TAC AAT GAT GTG CTT CAA CCG GGC GTT TGG AGT CCG GTA
    Leu Asn Tyr Asn Asp Val Leu Gln Pro Gly Val Trp Ser Pro Val
```

| | | | | | | | | | | | | | | | | |
|---|---|---|---|---|---|---|---|---|---|---|---|---|---|---|---|---|
| 662 | GCT Ala | GAA Glu | ACA Thr | ACA Thr | ATG Met | AGT Ser | GTG Val | GTG Val | TCA Ser | TTG Leu | CCT Pro | TTG Leu | TCT Ser | CAT His | TCT Ser | GGT Gly | GGG Gly |
| 713 | CAA Gln | TCT Ser | ACG Thr | GTA Val | TTT Phe | ATT Ile | CTA Leu | AAA Lys | GAC Asp | AGT Ser | GAA Glu | GGG Gly | GAT Asp | GTA Val | TTT Phe | GCT Ala | TAT Tyr |
| 764 | TTT Phe | GGT Gly | GAT Asp | ACA Thr | GGA Gly | CCT Pro | GAT Asp | GAA Glu | GTA Val | GAG Glu | AAA Lys | AGC Ser | TCG Ser | GCA Ala | ATG Met | AGG Arg | ACT Thr |
| 815 | GCA Ala | TGG Trp | TCT Ser | GTT Val | TTA Leu | GCT Ala | TTT Phe | CCT Pro | GTA Val | AAA Lys | CAA Gln | GGG Gly | AAG Lys | TTA Leu | AAG Lys | GGG Gly | ATT Ile |
| 866 | ATT Ile | ATT Ile | GAA Glu | GTT Val | TCT Ser | TTT Phe | AAC Asn | GAA Glu | ACC Thr | AAA Lys | CAA Gln | GAT Asp | AAA Lys | TCT Ser | TTG Leu | GGG Gly | GGA Gly |
| 917 | CAC His | TTA Leu | ACG Thr | CCA Pro | AAC Asn | TTT Phe | TGG Trp | GTT Val | AAA Lys | GTA Val | TTA Leu | AGT Ser | CTT Leu | GAA Glu | CAC His | GAC Asp | ATG Met |
| 968 | AAT Asn | GGC Gly | AAA Lys | GGC Gly | TCT Ser | TTA Leu | GAT Asp | CTA Leu | GTA Val | GTA Val | ATA Ile | GCC Ala | ATT Ile | AGC Ser | AAA Lys | ATC Ile | AAA Lys |
| 1019 | TAC Tyr | AGC Ser | TTA Leu | AAG Lys | AAT Asn | AGT Ser | GAT Asp | CCT Pro | GTA Val | AAA Lys | GTA Val | ATT Ile | ATT Ile | AAA Lys | CAC His | CAG Gln | TTA Leu |
| 1070 | GTA Val | GAA Glu | GTA Val | AAT Asn | GAC Asp | TTA Leu | GGT Gly | GTA Val | AAT Asn | TTC Phe | ATT Ile | TTT Phe | CCT Pro | GAG Glu | CAA Gln | GGT Gly | GAT Asp |
| 1121 | TCA Ser | TTG Leu | CAG Gln | TTT Phe | TAA *** | AAAAGTCATTGTAAAAGTGGATATGGTCAATACAAAGACCATATCCAC | | | | | | | | | | | |
| 1184 | GGATTTGTTTTTATCTCTTAAATCGTCGTTTCTATCTTTTTAAGCACGGCGATCTCATTGGGTACATCAATGTT | | | | | | | | | | | | | | | | |

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1257 base pairs
        ( B ) TYPE: nucleic acid
        ( C ) STRANDEDNESS: unknown
        ( D ) TOPOLOGY: unknown ( i i ) MOLECULE TYPE: protein ( i x ) FEATURE:
        ( A ) NAME/KEY: CDS
        ( B ) LOCATION: 143..1132

( x i ) SEQUENCE DESCRIPTION: SEQ ID NO:1:

| | | |
|---|---|---|
| AGTAGAACTA TCAAATTCTG TGGAGCATAC CGCTTATAAT TACCTTCTTA TCAATAGTCT | | 60 |
| TAAATATTTA ATACATCATT CATTTATCTC ATTGTATTAT CTGATTGAGC ACAAGGGTGT | | 120 |
| GCAGTATTAT TTAAGGTTGG AT ATG TTT AAA AAT AAA TTA GCA GTG TTA TTT | | 172 |
|                                   Met Phe Lys Asn Lys Leu Ala Val Leu Phe | | |
|                                    1                  5                           10 | | |
| ACG TGT TTG TCT GTA TTT TCT TTT TCG GCT CAA TCT GGG AGT TTT GAT | | 220 |
| Thr Cys Leu Ser Val Phe Ser Phe Ser Ala Gln Ser Gly Ser Phe Asp | | |
|                15                           20                               25 | | |
| ACC GTT ACG TTA GGG AGT AAA GGT GGG ATT CAA GAT GGT AAT TTA ACG | | 268 |
| Thr Val Thr Leu Gly Ser Lys Gly Gly Ile Gln Asp Gly Asn Leu Thr | | |
|            30                         35                            40 | | |
| GCT TTT TTA ATT AAA AGT GAG GCG GAT TCT AAT TTT GTT ATG CTT GAT | | 316 |
| Ala Phe Leu Ile Lys Ser Glu Ala Asp Ser Asn Phe Val Met Leu Asp | | |
|          45                        50                          55 | | |
| GCA GGT TCT GTT GTT AAT GGA TTA ATT GTT TCA GAG CAG AAA GGA GCG | | 364 |
| Ala Gly Ser Val Val Asn Gly Leu Ile Val Ser Glu Gln Lys Gly Ala | | |
|        60                       65                          70 | | |
| TTT AAA GAT ATT ACC GTC CCA GAT AGT TCG CCT TAC ACC AAA GTA GGT | | 412 |
| Phe Lys Asp Ile Thr Val Pro Asp Ser Ser Pro Tyr Thr Lys Val Gly | | |
| 75                     80                          85                          90 | | |
| TAC CTA TTA AAG GAT AGG ATT AAG GGC TAC TTT ATT AGT CAT GCT CAT | | 460 |
| Tyr Leu Leu Lys Asp Arg Ile Lys Gly Tyr Phe Ile Ser His Ala His | | |
|                          95                        100                         105 | | |
| TTA GAC CAT GTT GCT GGT TTA ATT ATC TCT TCT CCT GAT GAC AGT AAA | | 508 |
| Leu Asp His Val Ala Gly Leu Ile Ile Ser Ser Pro Asp Asp Ser Lys | | |
|                    110                        115                         120 | | |
| AAA CCG ATA TAT GGA TTA GCA GCG ACA AAT AAA GAT CTC ATG AAG AAT | | 556 |
| Lys Pro Ile Tyr Gly Leu Ala Ala Thr Asn Lys Asp Leu Met Lys Asn | | |
|               125                        130                         135 | | |
| TAC TTT AAT TGG TCA GCA TGG CCT AAT TTT GGT AAC AAA GGT GAA GGC | | 604 |
| Tyr Phe Asn Trp Ser Ala Trp Pro Asn Phe Gly Asn Lys Gly Glu Gly | | |
|       140                        145                         150 | | |
| TTT AAA CTG AAC AAA TAC AAT TAT GTG GAT CTT CAA CCG GGC GTT TGG | | 652 |
| Phe Lys Leu Asn Lys Tyr Asn Tyr Val Asp Leu Gln Pro Gly Val Trp | | |
| 155                  160                        165                         170 | | |
| AGT CCG GTA GCT GAA ACA ACA ATG AGT GTG GTG TCA TTG CCT TTG TCT | | 700 |
| Ser Pro Val Ala Glu Thr Thr Met Ser Val Val Ser Leu Pro Leu Ser | | |
|                    175                        180                         185 | | |
| CAT TCT GGT GGG CAA TCT ACG GTA TTT ATT CTA AAA GAC AGT GAA GGG | | 748 |
| His Ser Gly Gly Gln Ser Thr Val Phe Ile Leu Lys Asp Ser Glu Gly | | |
|                 190                        195                         200 | | |
| GAT GTA TTT GCT TAT TTT GGT GAT ACA GGA CCT GAT GAA GTA GAG AAA | | 796 |
| Asp Val Phe Ala Tyr Phe Gly Asp Thr Gly Pro Asp Glu Val Glu Lys | | |
|            205                        210                         215 | | |
| AGC TCG GCA ATG AGG ACT GCA TGG TCT GTT TTA GCT CCT TTT GTA AAA | | 844 |
| Ser Ser Ala Met Arg Thr Ala Trp Ser Val Leu Ala Pro Phe Val Lys | | |
|        220                        225                            230 | | |
| CAA GGG AAG TTA AAG GGG ATT ATT ATT GAA GTT TCT TTT ACC AAC GAA | | 892 |
| Gln Gly Lys Leu Lys Gly Ile Ile Ile Glu Val Ser Phe Thr Asn Glu | | |
| 235                  240                        245                         250 | | |
| ACC CCA GAT AAA TCT TTG TTT GGA CAC TTA ACG CCA AAC TGG TTA GTT | | 940 |
| Thr Pro Asp Lys Ser Leu Phe Gly His Leu Thr Pro Asn Trp Leu Val | | |
|                    255                        260                         265 | | |
| AAA GAA TTA AGT GTA CTT GAA GAC ATG AAT GGC AAA GGC TCT TTA AAA | | 988 |
| Lys Glu Leu Ser Val Leu Glu Asp Met Asn Gly Lys Gly Ser Leu Lys | | |
|                 270                        275                         280 | | |
| GAT CTA AAT GTA GCC ATA AGC CAC ATC AAA TAC AGC TTA AAG AAT AGT | | 1036 |
| Asp Leu Asn Val Ala Ile Ser His Ile Lys Tyr Ser Leu Lys Asn Ser | | |
|            285                        290                         295 | | |
| GAA GAT CCT AAA GTA ATT ATT AAA AAG CAG TTA GTA GAA GTA AAT GAC | | 1084 |

| Glu | Asp | Pro | Lys | Val | Ile | Ile | Lys | Lys | Gln | Leu | Val | Glu | Val | Asn | Asp | |
|-----|-----|-----|-----|-----|-----|-----|-----|-----|-----|-----|-----|-----|-----|-----|-----|---|
| | 300 | | | | 305 | | | | | | 310 | | | | | |

| TTA | GGT | GTA | AAT | TTC | ATT | TTT | CCT | GAG | CAA | GGT | GAT | TCA | TTG | CAG | TTT | 1132 |
|-----|-----|-----|-----|-----|-----|-----|-----|-----|-----|-----|-----|-----|-----|-----|-----|------|
| Leu | Gly | Val | Asn | Phe | Ile | Phe | Pro | Glu | Gln | Gly | Asp | Ser | Leu | Gln | Phe | |
| 315 | | | | | 320 | | | | | 325 | | | | | 330 | |

TAAAAAGTC ATTGTAAAAG TGGATATGGT CAATACAAAG ACCATATCCA CGGATTTGTT    1192

TTTATCTCTT AAATCGTCGT TTCTATCTTT TTAAGCACGG CGATCTCATT GGGTACATCA    1252

ATGTT    1257

PERIPLASMIC 3':5'-CYCLIC NUCLEOTIDE PHOSPHODIESTERASE AND RELATED METHODS FOR PRODUCING AND USING THE SAME

The present invention relates to a novel, substantially pure 3':5'-cyclic nucleotide phosphodiesterase which is found in the periplasm of certain bacteria, and which confers on those bacteria the ability to grow on, e.g., cAMP or cGMP as a sole carbon source. The present invention also relates to recombinant 3':5'-cyclic nucleotide phosphodiesterase, to isolated DNA encoding that enzyme, as well as to vectors, transformed hosts and methods for producing the recombinant enzyme.

3':5'-cyclic AMP (cAMP), a regulatory molecule involved in controlling gene transcription in various bacteria and in hormonally regulated processes in eucaryotic organisms, is synthesized from ATP by adenylate cyclase (E.C.4.6.1.1) and is degraded to 5'AMP (AMP) by cAMP phosphodiesterase (E.C.3.1.4.17) (Robison et al., *Cyclic Amp*, Academic Press, New York (1971); Botsford, Microbiological Reviews, 45:620–642 (1981); Francko, Advances in Cyclic Nucleotide Research, pp. 97–117 (1983); Ullman & Danchin, Advances in Cyclic Nucleotide Research, 15:1–52 (1983); Devroetes, Science, 245:1054–1058 (1989)). In enteric bacteria, cellular levels of cAMP apparently are regulated by the expression and activities of these two enzymes, which are cytoplasmic, and by excretion of excess cAMP into the growth medium. However, the role of cAMP phosphodiesterase in this regulation has not been completely resolved (Monard et al., Biochemical and Biophysical Research Communications, 35:584–591 (1969); Buettner et al., Journal of Bacteriology, 114:1068–1073 (1973); Alper & Ames, *Journal of Bacteriology*, 122:1081–1090 (1975); Saier et al., *Journal of Biological Chemistry*, 250:7593–7601 (1975); Botsford, 1981 supra; Botsford, Journal of Bacteriology, 160:826–830 (1984)). Alternatively, cAMP phosphodiesterase might function as a defense against extracellular cAMP, which can cause growth inhibitory and lethal effects in various Gram-negative bacteria. A role in defence against cAMP might require that the enzyme be extracellular in bacteria, as it is in the cellular slime mold *Dictyostelium discoideum*.

In a recent paper, we described the novel ability of the symbiotic bioluminescent bacterium *Vibrio fischeri* to utilize cAMP as a sole source of carbon and energy for growth. This ability correlates with, and apparently depends on, the synthesis by *V. fischeri* of a 3':5'-cAMP phosphodiesterase of exceptionally high activity in the periplasmic space, a novel cellular location for this enzyme (Dunlap et al., J. Gen. Microbiol. 138:115–123 (1992)). The cellular location and high activity of this enzyme in *V. fischeri* indicate that a role for this enzyme in regulation of cytoplasmic cAMP levels is unlikely. These attributes, however, are consistent with a role in defense against extracellular cAMP. Alternatively, the periplasmic CPDase of *V. fischeri* could function in degradation and scavenging of free cAMP (Barfield et al., *Microbiol. Enzymes in Aquatic Environment*, Springer Berlay, 1991, pp. 239–248), or possibly in some aspect of cAMP-mediated biochemical interactions between *V. fischeri* and its animal hosts (Dunlap et al., supra).

It would therefore be desirable to produce commercially useful amounts of 3':5'-cyclic nucleotide phosphodiesterases in a substantially pure form, either from its native source or as a recombinant enzyme. Substantially pure enzyme could be used. e.g., as a component in an assay for determining the presence and/or amount of cAMP or cGMP, or to eliminate cAMP or cGMP from environmental, biological, and biomedical samples containing the same.

SUMMARY OF THE INVENTION

In accordance with the present invention, there is provided a novel, substantially pure periplasmic 3':5'-cyclic nucleotide phosphodiesterase, in particular, 3':5'-cAMP and cGMP phosphodiesterase. This enzyme is obtainable from gram negative bacterium such as *Vibrio fischeri*.

This enzyme has very high specific activity and narrow substrate specificity and confers on its source organism the ability to grow on cAMP or cGMP. Also disclosed are methods for identifying and obtaining such periplasmic proteins from other gram negative bacteria.

The present invention further provides means for obtaining the recombinant enzyme as well as the isolated DNA encoding such 3':5'-cyclic nucleotide phosphodiesterases, as well as recombinant vectors, transformed hosts and methods for producing the recombinant enzyme.

BRIEF DESCRIPTION OF THE DRAWINGS

FIG. 4. Nucleotide sequence and deduced amino acid (SEQ ID NO:1) translation of the *V. fischeri* cpdP gene. Possible Pibnow box (−10) and ribosome binding (SD) regions are underlined, as is a twelve base pair inverted repeat adjacent to the location where a −35 region would be expected. The arrow between amino acid residues 22 and 23 indicates the cleavage site for the CpdP leader peptide. A possible rho-independent terminator, with a free energy of −21.2 kcal/mol, at the end of the cpdP coding region is underlined.

DETAILED DESCRIPTION OF THE INVENTION

Figure 1:
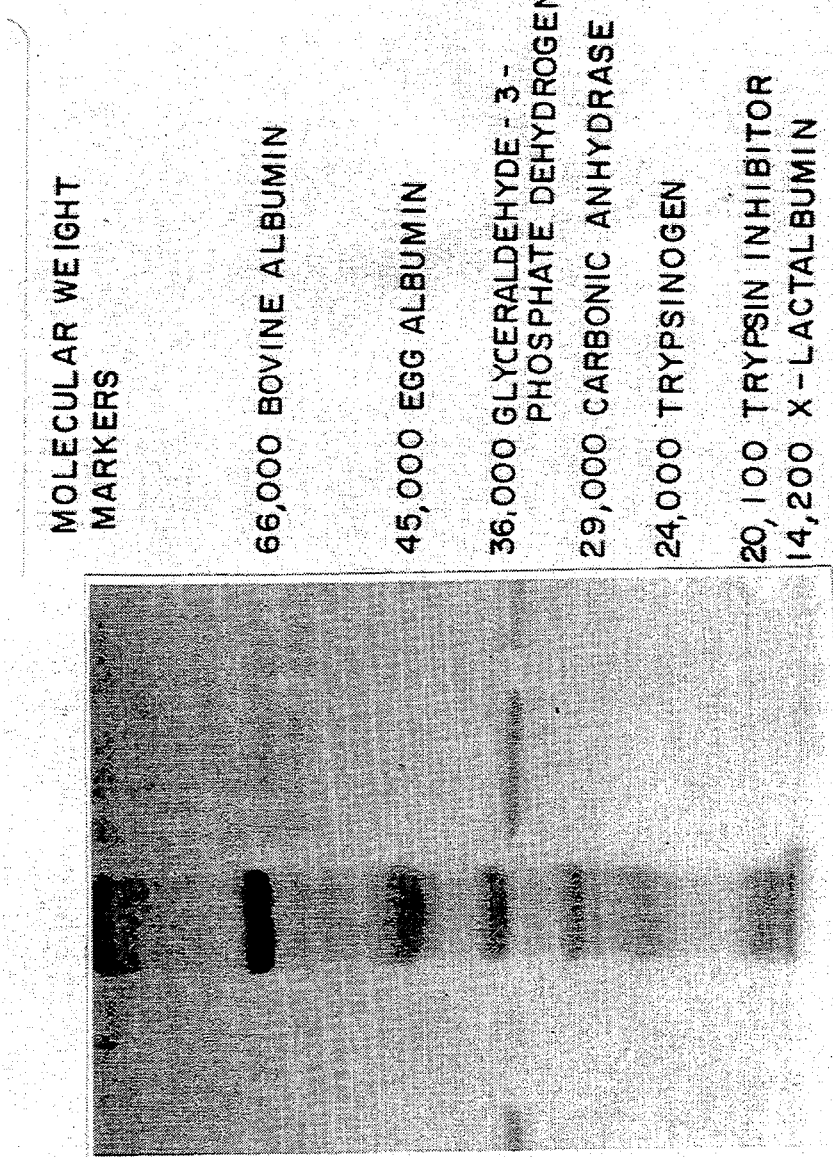
FIG. 1. Sodium dodecyl sulfate (SDS) polyacrylamide gel electrophoresis (PAGE) of 3':5'-cyclic AMP phosphodiesterase (CpdP, 34 kDa) purified from *V. fischeri* MJ-1 by the anion exchange and affinity chromatography procedure described in Example 1. 30 μl of sample, containing 10 μg total protein, was loaded and electrophoresed under the conditions described on the drawing. Other proteins, seen near the top of the lane, comprise less than 10% of the total loaded protein.

In accordance with one embodiment of the present invention, substantially pure periplasmic 3':5'-cyclic nucleotide phosphodiesterase, such as 3':5'-cyclic AMP or GMP phosphodiesterase, may be obtained by culturing the source organism, such as *Vibrio fischeri*, and recovering the enzyme from the periplasm of the cell.

The enzyme of the present invention is a periplasmic enzyme which confers on the bacterium in which it is expressed the ability to grow on cAMP or cGMP as a sole carbon source. This periplasmic enzyme is believed to be present in a number of gram negative bacteria, including *Vibrio fischeri* and *Serratia marcescens*. Gram negative bacteria which contain such periplasmic enzymes may be identified by simply culturing the candidate bacterium on minimal media containing cAMP or cGMP as the sole carbon source. Survivors of these cultures may be assayed for the presence of the enzyme as described in Dunlap et al., supra, the disclosure of which is incorporated by reference herein.

One source of this enzyme, *Vibrio fischeri*, which harbors 3':5'-cAMP phosphodiesterase, is available from a number of sources, including the American Type Culture Collection under Accession nos. 7744, 25918, 33765, 33983 and 33984.

For recovering the enzyme of the present invention, the bacterium, such as *V. fischeri*, may be grown using any suitable technique such as those described in Dunlap et al., supra. After the cells have been grown, the periplasmic protein fraction is obtained by, for example, the chloroform shock method described by Ames et al., *J. Bacteriol.*, 160:1181-1183 (1984), the disclosure of which is incorporated by reference herein. One can then isolate the target protein by a number of approaches such as ammonium sulfate precipitation followed by one or more of the following: acetone precipitation, affinity chromatography, anion exchange chromatography and the like.

In general, the protein is at least greater than about 10% pure, preferably greater than about 50% pure, and most preferably greater than about 90% pure compared to that found in the source organism. Percent purity may be determined by, for example, visualization of the protein on SDS-PAGE and quantification thereon by scanning densitometry, thereby indicating the protein's relative percent purity with respect to the presence of any other proteins not eliminated in the purification procedure. Therefore, substantially pure at the 50% level means that the protein accounts for at least half of the total protein present in a sample, and substantially pure at the 90% level means that the protein accounts for at least nine-tenths of the total protein present in a sample. Absolute fold purity can be quantified by determining the specific activity (i.e., the enzymatic activity per mg protein per minute) of the protein at a given step in the purification process with reference to its specific activity in whole cells.

The enzyme of the present invention may also be obtained by recombinant techniques whereby the DNA coding for the enzyme is isolated, inserted into a suitable vector and transformed into a host cell, the host cell being cultured under conditions suitable for expression of the enzyme.

In general, the recombinant enzyme can be obtained from any gram negative bacterium producing it by procedures essentially identical to those described herein (see Example 3), i.e., through the process of isolating the DNA encoding it by the procedures described in Example 3, inserting that DNA into a suitable vector such as pBR322 or pACYC184 or lambda phage-based vectors, transforming or transducing a suitable host cell line such as *E. coli*, and culturing the transformed or transduced host cells under conditions suitable for expression of the enzyme such as on minimal media containing cAMP or cGMP as the sole carbon source.

The following examples are given to illustrate embodiments of the present invention as it is presently preferred to practice. It will be understood that these examples are illustratative, and that the invention is not to be considered as restricted thereto except as indicated in the claims.

EXAMPLE 1

Purification of periplasmic 3':5'-cyclic AMP phosphodiesterase from *V. fischeri* MJ-1. Growth and harvesting of cells. To obtain the periplasmic 3':5'-cAMP phosphodiesterase protein, a one-liter culture of *V. fischeri* minimal medium (VFM) is prepared, composed of 300 mM NaCl, 10 mM KCl. 50 mM $MgSO_4$, 10 mM $CaCl_2$, 5 mM $NH_4Cl$, 0.3 mM α-glycerophosphate and 50 mM HEPES (N-2-hydroxy-ethylpiperazine-N'-2-ethanesulfonic acid), pH 7.5, 20 mg ferric ammonium citrate per liter, and glucose (10 mM). The culture was inoculated with 10 ml of VFM-glucose-grown cells at a cell density (optical density at 660 nm, $OD_{660}$) of 0.6 to 0.8. The cells were grown at 28° C. with shaking (50 rpm) to saturation (uncorrected $OD_{660}$ of 1.1), and then allowed to sit without shaking for 2 hrs. The culture was then divided among four 500 ml centrifugation bottles, and the cells were harvested by centrifugation at 10,000 rpm for 5 min at 4° C. in a Sorvall RC-2B centrifuge using a GS rotor.

Chloroform shock. Periplasmic proteins were released from cells by the chloroform shock method described by Ames at al., supra. The cell pellets were resuspended and combined in a total volume of 50 ml of 10 mM Tris buffer (tris[hydroxymethyl]aminomethane) pH 8.0 (22° C.) in a 250 ml centrifuge bottle. To the cell suspension, 10 ml of chloroform was added, and the suspension was mixed by gentle swirling and inversion and then allowed to sit at room temperature for 15 min with occasional inversion. 100 ml of 10 mM Tris buffer (pH 8.0, 22° C.) was then added, the suspension was mixed gently by inversion, and then centrifuged at 10,000 rpm (4° C.) for 20 min. The aqueous phase (approximately 140 ml to 150 ml) was then removed, taking care to avoid the cell pellet and chloroform.

Ammonium sulfate precipitation. Sufficient (approximately 250 ml) 50 mM Tris buffer (pH 8.0, 22° C.) was added to the periplasmic extract obtained above to raise its volume to 400 ml. The solution was stirred on ice and ammonium sulfate was added, as described by Cooper, *The Tools of Biochemistry* (1977), to give 30, 50 and 65% saturation, with a 30 min. equilibration for each addition of ammonium sulfate. Proteins precipitating with each of these ammonium sulfate additions were collected by centrifugation at 10,000 rpm (0° C.) for 10 min, followed by resuspension in 10 ml of 10 mM Tris buffer (pH 8.0, 22° C.). In our previous study (Dunlap et al., supra), ammonium sulfate fractionation or periplasmic proteins from *V. fischeri* MJ-1 gave small (approximately 4-fold) purification of the 3':5'cAMP phosphodiesterase that was effective in establishing the substrate specificity of the enzyme.

Affinity chromatography. The 3':5'-cAMP phosphodiesterase was further purified using dye affinity ligand chromatography. The 65% ammonium sulfate fraction, which contained most of the 3':5'-cAMP phosphodiesterase activity, was applied to a 10 ml disposable Poly-Prep chromatography column (Bio-Rad Laboratories, Richmon, Calif.) containing 1 ml of Cibacron Blue agarose (Sigma Chemical Co., St. Louis, Mo.). The column material had been equilibrated with 100 mM MgSO4 at 4° C. as follows. For hydration, 0.2 g of Cibacron Blue agarose was mixed with 2 ml of deionized water and allowed to sit for 15 min. The hydrated agarose was then trapped on a filter (0.2 μM pore size), washed with 100 ml of deionized water, run dry, washed with 15 ml 100 mM MgSO4, run dry, and then resuspended in 3 ml of 100 mM MgSO4 and loaded into the column. To pack the column, 20 ml of 100 Mm MgSO4 was then passed through the agarose, without running the column dry, and the sample was added slowly by applying it down the side of the column. The column was then washed with 5 ml of 1 M KCl in 50 mM Tris base (pH 10.3). The 3':5'-cAMP phosphodiesterase was then eluted in 5 ml of the wash solution (1 M KCl in 50 mM Tris base) containing 10 mM adenosine. The maximum possible flow rate (approximately 20 ml/hr) was used in all cases. Adenosine was used to elute the 3':5'-cAMP phosphodiesterase from the column (instead of cAMP or AMP) because adenosine inhibited 3':5'-cAMP phosphodiesterase activity effectively and did not contribute phosphate, which would interfere with the assays for 3':5'-cAMP phosphodiesterase enzyme.

Anion exchange chromatography. To remove salts and to lower the pH of the solution, the Cibacron Blue agarose column eluate was then dialyzed in Spectra/Por membrane tubing (m.w. cutoff 3,500)(Spectrum Medical Industries, Los Angeles, Calif.) (prepared as described by Sambrook et al., Molecular Cloning, Cold Spring Harbor (1989)), with three changes (3 hrs each) of 1.5 liters of 10 mM imidazole (pH 6.0) at 4° C., with periodic pH correction using 1 N HCl. The dialyzed material was then applied to a 10 ml disposable Bio-Rad Poly-Prep chromatography column containing 1.5 ml of DEAE-Sephacel (Sigma). The choice of pH 6.0 was made based on the calculated pI of 5.49 for the mature protein. The DEAE-Sephacel had been equilbrated with 10 mM imidazole (pH 6.0) at 4° C. as follows. The hydrated column material was washed with deionized water, washed with 0.1 N HCl, incubated with 0.1 N HCl, gently centrifuged (<500 rpm) to permit the solution to be removed, and then repeatedly resuspended with 10 mM imidazole (pH 7.0) and spun to equilibrate the pH to 6.0. Equilibrated DEAE Sephacel was loaded into the column and packed at 4° C. with 30 ml of 10 mM imidazole at pH 6.0. After applying the same sample to the column and washing with 5 ml of the imidazole buffer, the 3':5'-cAMP phosphodiesterase was eluted with 5 ml of 0.2 M Nacl in 10 mM imidazole, pH 6.0. After elution, the 5 ml sample was concentrated to 1 ml using a Centricell 20 (Polysciences, Inc., Warrington, Pa.) centrifugal ultrafilter (nominal molecular weight cutoff 10,000 Daltons), resuspended in 15 ml of 10 mMol imidazole, pH 6.0, in 20% (w/v) glycerol, and concentrated to 1 ml for storage at −70° C. The maximum possible flow rate (approximately 10 ml/hr) was used in all cases.

Protein assay, 3':5'-cAMP phosphodiesterase assay, and polyacrylamide gel electrophoresis of proteins. Protein content of samples was determined by the method of Bradford, Analyt. Biochem., 72:248–254 (1977), using bovine serum albumin as the standard and a Coomassie brilliant blue G-520 protein assay reagent (Pierce, Rockford, Ill.) essentially in accordance with the manufacturer's instructions.

Activity of 3':5'-cAMP phosphodiesterase in samples was measured with the method of Cheung essentially as described by Dunlap et al. (1992), supra, using cAMP as the substrate, 5'-nucleotidase to cleave the generated 5'AMP, and with the phosphate released determined by the method of Fiske and SubbaRow (J. Biol. Chem., 66:375–400 (1925)).

Proteins were visualized by SDS polyacrylamide gel electrophoresis, using a Hoefer SE250 (Hoefer Scientific Instruments, San Francisco, Calif.) mini gel apparatus and following the procedure described by Laemmli (Nature, 227:680–685 (1970)). As can be seen from FIG. 1, the 3':5'-cAMP phosphodiesterase has a molecular weight of about 34,000 on SDS-PAGE. The above protocol gives protein that is approximately 1000-fold purified compared to whole cells and that on SDS-PAGE looks to be about 90% pure.

EXAMPLE 2

Cold Acetone Purification of 3':5'-cAMP phosphodiesterase

Whole cells were pelleted, washed and resuspended in buffer and exposed to chloroform to release periplasm contents as described in Example 1. The supernatant, containing the periplasm contents, was fractionated with ammonium sulfate, as described in Example 1, and the 70% fraction was treated with cold acetone. Specifically, to the 70% ammonium sulfate fraction on ice, 0.75 volume (7.5 ml) of acetone at −20° C. was added, the solution was mixed by inversion a few times and placed at −20° C. for 45 min. The solution was then spun in a Sorvall RC-2B centrifuge in an SS-34 rotor for 5 min at −5° C. to −10° C. The pellet was resuspended in 10 ml of 10 mM Tris buffer at pH 8.0 (22° C.), assayed, found to have no activity, and discarded. 10 ml cold acetone (now 1.75 volumes of acetone) was then added to the supernatant, which contained the activity, and the incubation and spin were repeated. The pellet, which contained the activity, was resuspended in 10 ml of 10 mM Tris buffer at pH 8.0 (room temp.), assayed, and examined by SDS-polyacrylamide gel electrophoresis.

| | |
|---|---|
| Whole cells: | 2.1 μmol Pi released/min/mg/protein |
| Periplasm extract: | 29 |
| Ammonium sulfate 70% fraction: | 109 |
| Acetone | 280 |

We interpret these results as indicating a 100-fold purification of the protein.

Figure 2:
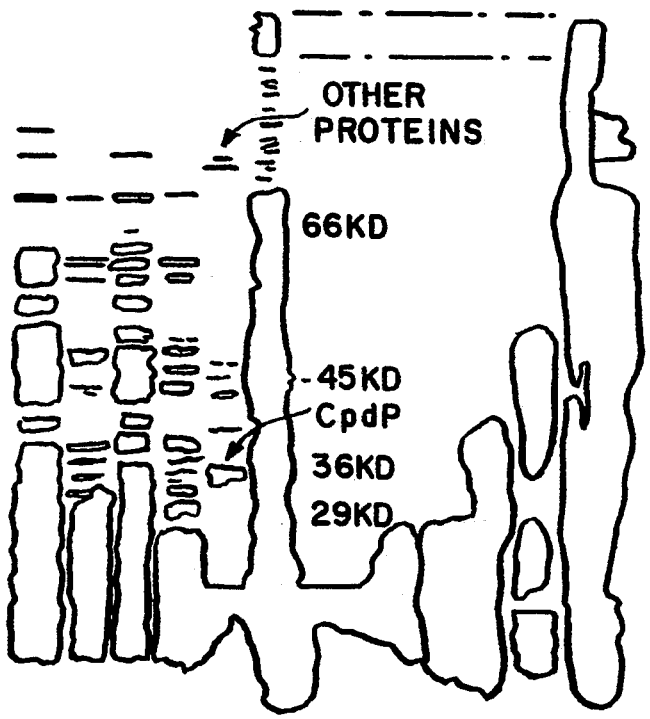
FIG. 2. Sodium dodecyl sulfate (SDS) polyacrylamide gel electrophoresis (PAGE) of 3':5'-cyclic AMP phosphodiesterase (CpdP, 34 kDa) purified from *V. fischeri* MJ-1 by the cold acetone procedure described in Example 2. 30 μl of sample, containing 80 μg total protein, was loaded and electrophoresed under the conditions described on the drawing. Other proteins, seen near the top of the lane, comprise less than 50% of the total loaded protein.

The gel, FIG. 2, was loaded with 30 μl of protein suspension, containing 80 μg of protein. Visual inspection of the gel indicates that protein is approximately 50% pure. Scanning densitometry analysis could also be used to quantify the protein and its percent purity.

EXAMPLE 3

Cloning of a Periplasmic 3':5'-Cystic Nucleotide

Phosphodiesterase Gen To isolate the *V. fischeri* gene encoding periplasmic 3':5'cAMP phosphodiesterase, cells of *E. coli* AG-1 (Bullock et al., Biotechniques, 5:376-379 (1987)) were transformed with a gene library of *V. fischeri* MJ-1 (Rudy et al., *Biol. Bull.*, 151:574-586 (1976)) chromosomal DNA constructed in pSUP102 (Simon et al., Meth. Enzymol., 118:640-659 (1986)) and plated on *E. coli* minimal medium (50 mM Tris-HCl, 50 mM NaCl, 1 mM $M_gSO^4$, 1 mM $CaCl_2$, 0.05 mM thiamine, 0.005% yeast extract (Difco), and 0.005% tryptone (Difco), pH 7.4, 15 g/l agar) agar plates containing cAMP (5 mM) as the sole carbon and energy source and chloramphenical (30 μg/ml). The genomic library of DNA from *V. fischeri* MJ-1 was prepared essentially as described by Sambrook et al. (1989) and Silhavy et al. (*Experiments with Gene Cloning*, Cold Spring Laboratory (1986)). Purified chromosomal DNA was partially digested with Sau3A1, size fractionated on a 0.7% agarose-TAE gel, and the portion of the gel containing the 10-15 kb size range of DNA was isolated. The DNA was electroeluted from the gel slice, purified by phenol extraction and ethanol precipitation, and then ligated into the BamH1 site of pSUP102 (Simon et al., Meth. Enzymol., 118:640-659 (1986)). The library was recovered by transformation of *E. coli* AG-1, with selection on LB agar (Silhavy et al., supra) containing chloramphenicol (30 μg/ml). Initial attempts at isolating the gene, by plating the transformed *E. coli* AG-1 cells on ECM-cAMP agar supplemented with $K_2HPO_4$ and $NH_4Cl$, were unsuccessful. In other work, however, we had noted that growth of *V. fischeri* on cAMP was suppressed somewhat in minimal medium supplemented with $K_2HPO_4$ and $NH_4Cl$ compared to minimal medium lacking these constituents. In accordance with this observation, the transformed *E. coli* AG-1 cells were plated on ECM-cAMP lacking $K_2HPO_4$ and $NH_4Cl$. In this case, several colonies arose in two days at 37° C.; all were found by restriction endonuclease digestion of their plasmid DNA to contain a similar 10-13-kilobase (kb) region of *V. fischeri* DNA. One clone, pMER120, which contained approximately 12 kb of *V. fischeri* DNA, was chosen for further study.

AG-1 containing pMER120 grew well in ECM-cAMP broth (lacking $K_2HPO_4$ and $NH_4Cl$), whereas AG-1 containing pSUP102 did not grow in this medium but did grow in ECM containing glucose, $K_2HPO_4$ and $NH_4Cl$. When *E. coli* AG-1 was re-transformed with pMER120 and plated on selective medium, an equal number of colonies arose on ECM-cAMP agar plates containing chloramphenical as arose on LB agar plates containing chloramphenicol. Consistent with growth on cAMP, AG-1 containing pMER120 expressed periplasmic CPDase activity, as determined by enzyme assays on intact cells (Dunlap et al., supra), at levels similar to those in *V. fischeri*. *E. coli* AG-1 containing pSUP102, however, exhibited no detectable periplasmic CPDase activity. By these criteria, we ascertained that the cloned *V. fischeri* DNA in pMER120 contained the gene encoding periplasmic CPDase.

We designate the gone for the *V. fischeri* periplasmic CPDase provisionally as cpdP, with P as a mnemonic for periplasmic. This designation accords with the designation given the gene (cpdA), which has not yet been cloned, of the cytoplasmic CPDase of *Salmonella typhimurium* (Alper and Ames, supra) and with the designation given the cloned gone (cpdB) encoding the periplasmic 2':3'-cAMP phosphodiesterase of *E. coli* (Beacham and Garrett, J. Gen. Micro., 119:31-34 (1980)).

Figure 3:
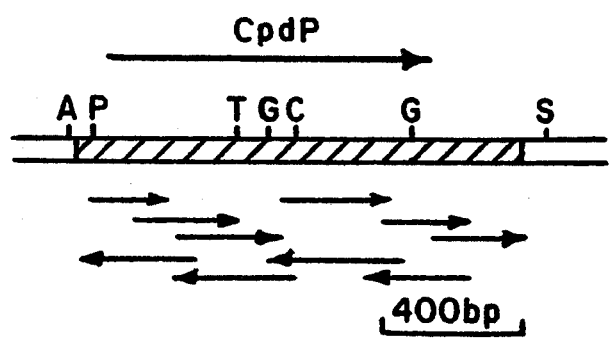
FIG. 3. Sequencing strategy and partial restriction mad of the *V. fischeri* cpdP gene. The large arrow indicates the extent and direction of the cpdP gene. The solid region represents *V. fischeri* MJ-1 chromosomal DNA, and the open regions represent the vector, pMER013. Small arrows indicate the direction and extent of sequences obtained with each primer. The restriction sites are: A, ApaI; I, NciI; G, BglII; P, SspI; S, SalI; and T, BstI.

Nucleotide sequence of the *V. fischeri* cpdP gene. The DNA sequence of the 1.26 kb of *V. fischeri* DNA contained in pMER013 [pGEM ®-7Zf(+)] was determined bidirectionally with SP6 and T7 primers and with primers designed for regions internal to the cloned DNA by the dideoxy termination method of Sanger et al. (*Proc. Natl. Acad. Sci.*, 74:5463-5467 (1977)). A partial restriction map and the sequencing strategy are shown in FIG. 3. DNA sequence analysis was performed with the MacDNASIS Pro 1.01 package (national Bioscience, Plymouth, Minn.) Translation of the DNA sequence revealed one open reading frame, beginning at position 143 (ATG) and ending at position 1133 (TAA), specifying a protein of 330 amino acid residues and a deduced molecular weight of 36,087 (FIG. 4). The portion of the 12-kb insert DNA encoding CpdP (pMER120) was defined to 1.26 kb (pMER013) by standard subcloning and endonuclease III digestion procedures.

The recombinant enzyme can be purified to a similar degree of purity by the methods described in Examples 1 and 2.

---

What is claimed is:

1. Isolated DNA coding for a periplasmic 3':5'-cyclic AMP phosphodiesterase obtainable from *Vibrio fischeri*.

2. The isolated DNA of claim 1, wherein said isolated DNA hybridizes to the nucleotide sequence of FIG. 4 (SEQ ID NO:1).

3. The isolated DNA of claim 1, wherein said isolated DNA comprises the DNA of FIG. 4 (SEQ ID NO:1).

4. A cloning vector which comprises the isolated DNA of claim 1.

5. A host cell transformed with the cloning vector of claim 4.

6. The isolated DNA of claim 1 wherein the phosphodiesterase has a molecular weight of about 34,000 on SDS-PAGE.

7. A cloning vector which comprises the isolated DNA of claim 3.

8. Isolated DNA coding for a periplasmic 3':5'-cyclic nucleotide phosphodiesterase represented by the amino acid sequence of FIG. 4.

9. The isolated DNA of claim 8 wherein the phosphodiesterase has a molecular weight of about 34,000 on SDS-PAGE.

10. A cloning vector comprising the isolated DNA of claim 8.

11. A host cell transformed with the cloning vector of claim 10.

12. A method of producing a recombinant periplasmic 3':5'-cyclic AMP phosphodiesterase obtainable from *Vibrio fischeri*, comprising culturing *E. coli* cells transformed with a vector containing DNA coding for the phosphodiesterase on cAMP in the absence of $K_2HPO_4$ and $NH_4Cl$.

13. The method of claim 12 wherein the DNA coding for the phosphodiesterase comprises the DNA of FIG. 4.

14. The method of claim 12 wherein the DNA codes for the phosphodiesterase represented by the amino acid sequence of FIG. 4.

15. Isolated DNA coding for a periplasmic 3':5'-cyclic nucleotide phosphodiesterase obtainable from *Vibrio fischeri*, wherein said isolated DNA hybridizes to the nucleotide sequence of FIG. 4.

16. The isolated DNA of claim 15 wherein the phosphodiesterase has a molecular weight of about 34,000 on SDS-PAGE.

17. A cloning vector which comprises the isolated DNA of claim 15.

18. A host cell transformed with the cloning vector of claim 17.

* * * * *